(12) United States Patent
Drey et al.

(10) Patent No.: US 12,048,641 B2
(45) Date of Patent: *Jul. 30, 2024

(54) HEEL PROTECTOR AND CORRESPONDING REHABILITATION SYSTEMS AND METHODS FOR USING THE SAME

(71) Applicant: Medline Industries, LP, Northfield, IL (US)

(72) Inventors: Michelle Drey, Chicago, IL (US); Bruce Shapiro, Deerfield, IL (US)

(73) Assignee: Medline Industries LP, Northfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/142,920

(22) Filed: May 3, 2023

(65) Prior Publication Data
US 2023/0270577 A1    Aug. 31, 2023

Related U.S. Application Data

(60) Continuation of application No. 16/993,737, filed on Aug. 14, 2020, now Pat. No. 11,752,023, which is a division of application No. 15/892,186, filed on Feb. 8, 2018, now Pat. No. 10,779,981, which is a continuation of application No. 14/468,872, filed on Aug. 26, 2014, now Pat. No. 9,980,845.

(51) Int. Cl.
*A61F 5/01* (2006.01)
*A61F 5/058* (2006.01)

(52) U.S. Cl.
CPC ........ *A61F 5/0111* (2013.01); *A61F 5/05816* (2013.01)

(58) Field of Classification Search
CPC .... A61F 5/0111; A61F 5/05816; A61F 5/058; A61F 5/05; A61F 5/01; A61F 5/0127; A61F 5/012; A61F 5/0195
See application file for complete search history.

(56) References Cited

U.S. PATENT DOCUMENTS

| 3,011,494 A | 12/1961 | McGowan |
| 1,562,454 A | 11/1965 | Jankins |
| 3,216,417 A | 11/1965 | Posey |

(Continued)

FOREIGN PATENT DOCUMENTS

| WO | 94/01071 | 1/1994 |

OTHER PUBLICATIONS

"Calibrated V-Lok Cuff", Calibrated V-Lok Cuff Specification Publication; Publicly available more than one year prior to the filing date of the present application.; Printed Sep. 2012; p. 1.

(Continued)

*Primary Examiner* — Tarla R Patel
(74) *Attorney, Agent, or Firm* — Philip H. Burrus, IV

(57) ABSTRACT

A device (100) includes a leg engaging section (101) and a foot engaging section (102) intersecting at a heel receiver (103). The leg engaging section and the foot engaging section define a leg insertion aperture (104). A compressible cushion layer (402) is disposed at least in the leg engaging section. At least one bolster tube (401) is disposed interior the leg engaging section. The bolster tube (401) can be selectively removable through one or more apertures (1105, 1106).

20 Claims, 12 Drawing Sheets

(56) References Cited

U.S. PATENT DOCUMENTS

| | | |
|---|---|---|
| 3,279,459 A | 10/1966 | Schenker |
| 3,490,450 A | 1/1970 | Gardner |
| 3,648,291 A | 3/1972 | Pankers |
| 3,674,023 A | 7/1972 | Mann |
| 3,693,619 A | 9/1972 | Williams |
| D225,472 S | 12/1972 | Lowrey et al. |
| 3,721,237 A | 3/1973 | Alessio |
| 3,905,135 A | 9/1975 | Debusk |
| D239,058 S | 3/1976 | Gaylord, Jr. |
| 3,955,565 A | 5/1976 | Johnson, Jr. |
| 4,135,504 A | 1/1979 | Spann |
| 4,186,738 A | 2/1980 | Schleicher et al. |
| 4,266,298 A | 5/1981 | Graziano |
| D261,821 S | 11/1981 | Hubbard et al. |
| D268,365 S | 3/1983 | Malkin |
| 4,441,493 A | 4/1984 | Nirschl |
| 4,445,505 A | 5/1984 | Labour |
| 4,573,482 A | 3/1986 | Williams, Jr. |
| 4,597,395 A | 7/1986 | Barlow et al. |
| 4,624,244 A | 11/1986 | Taheri |
| 4,730,610 A | 3/1988 | Graebe |
| RE32,680 E | 5/1988 | Pompa |
| 4,781,133 A | 11/1988 | Hanyu et al. |
| 4,947,834 A | 8/1990 | Kartheus et al. |
| 4,972,832 A | 11/1990 | Trapini et al. |
| 5,052,128 A | 10/1991 | Lonardo |
| 5,085,210 A | 2/1992 | Smith, III |
| 5,226,245 A | 7/1993 | Lamont |
| D338,067 S | 8/1993 | Luber et al. |
| D343,002 S | 1/1994 | Gauvry |
| 5,288,286 A | 2/1994 | Davis et al. |
| D352,381 S | 11/1994 | Rose |
| 5,367,789 A | 11/1994 | Lamont |
| 5,435,009 A | 7/1995 | Schild et al. |
| 5,449,339 A | 9/1995 | Drennan |
| 5,464,385 A | 11/1995 | Grim |
| 5,479,471 A | 12/1995 | Buckland |
| 5,511,552 A | 4/1996 | Johnson |
| 5,588,954 A | 12/1996 | Ribando |
| 5,609,570 A | 3/1997 | Lamont |
| 5,626,556 A | 5/1997 | Tobler et al. |
| 5,649,954 A | 7/1997 | McEwen |
| 5,660,182 A | 8/1997 | Kuroshaki et al. |
| 5,827,211 A | 10/1998 | Sellinger |
| 5,833,639 A | 11/1998 | Nunes et al. |
| 5,868,690 A | 2/1999 | Eischen, Sr. |
| D410,746 S | 6/1999 | Klein |
| 6,080,120 A | 6/2000 | Sandman et al. |
| 6,126,627 A | 10/2000 | Brennan |
| 6,152,893 A | 11/2000 | Pigg et al. |
| 6,277,087 B1 | 8/2001 | Hess et al. |
| 6,308,713 B1 | 10/2001 | Coleman |
| 6,322,530 B1 | 11/2001 | Johnson, Jr. et al. |
| 6,338,723 B1 | 1/2002 | Carpenter et al. |
| D453,969 S | 2/2002 | Callsen et al. |
| D455,836 S | 4/2002 | Lammers |
| 6,572,573 B1 | 6/2003 | Klein |
| 6,640,810 B1 | 11/2003 | Callsen et al. |
| 7,004,920 B2 | 2/2006 | Fareed |
| D517,306 S | 3/2006 | Hoeft |
| 7,052,479 B2 | 5/2006 | Drennan |
| 7,115,105 B2 | 10/2006 | Cropper |
| D542,921 S | 5/2007 | Ponsi et al. |
| D544,101 S | 6/2007 | Kistner |
| 7,252,647 B1 | 8/2007 | Hely |
| D551,354 S | 9/2007 | McBarnett et al. |
| 7,276,037 B2 | 10/2007 | Ravikumar |
| 7,329,232 B2 | 2/2008 | Moses et al. |
| D571,083 S | 6/2008 | Mohammad |
| 7,455,651 B2 | 11/2008 | Mollica |
| 7,458,948 B2 | 12/2008 | Drennan |
| 7,798,984 B2 * | 9/2010 | Ponsi .................... A61F 5/012 |
| | | 602/61 |
| 8,152,749 B2 | 4/2012 | Ponsi et al. |
| 8,216,165 B2 | 7/2012 | Ravikumar et al. |
| 8,241,263 B2 | 8/2012 | Mills |
| 8,251,932 B2 | 8/2012 | Fout |
| 8,435,199 B2 * | 5/2013 | Ponsi .................... A61F 5/0111 |
| | | 602/65 |
| D697,628 S | 1/2014 | Drey et al. |
| 8,628,487 B2 | 1/2014 | Ponsi |
| 8,894,598 B2 | 11/2014 | Ponsi et al. |
| D731,158 S | 6/2015 | Backus |
| D749,744 S | 2/2016 | Drey |
| 9,439,826 B2 * | 9/2016 | Drey ..................... A61H 9/005 |
| 9,844,484 B2 * | 12/2017 | Noskowicz .......... A61H 9/0092 |
| 9,980,845 B2 * | 5/2018 | Drey .................... A61F 5/0111 |
| 10,292,895 B2 * | 5/2019 | Drey .................... A61F 5/05816 |
| 10,667,983 B2 * | 6/2020 | Noskowicz .......... A61H 9/0092 |
| 10,779,981 B2 * | 9/2020 | Drey .................... A61F 5/0111 |
| 11,273,095 B2 * | 3/2022 | Drey ..................... A61H 9/0092 |
| 11,752,023 B2 * | 9/2023 | Drey .................... A61F 5/05816 |
| | | 128/845 |
| 11,771,616 B2 * | 10/2023 | Noskowicz ............ A61H 9/005 |
| | | 601/151 |
| 11,793,710 B2 * | 10/2023 | Drey .................... A61F 5/05816 |
| 2001/0051240 A1 | 12/2001 | Denis |
| 2003/0168063 A1 | 9/2003 | Gambone et al. |
| 2004/0111048 A1 | 6/2004 | Jensen et al. |
| 2004/0236261 A1 | 11/2004 | McCarthy |
| 2005/0131321 A1 | 6/2005 | Ravikumar |
| 2005/0171461 A1 | 8/2005 | Pick |
| 2005/0192524 A1 | 9/2005 | Lipshaw et al. |
| 2007/0032773 A1 | 2/2007 | Magee |
| 2007/0033697 A1 | 2/2007 | Soldwedel |
| 2007/0074427 A1 | 4/2007 | Ponsi et al. |
| 2007/0197988 A1 | 8/2007 | Bieling |
| 2007/0282230 A1 | 12/2007 | Valderrabano |
| 2008/0022559 A1 | 1/2008 | Ponsi |
| 2009/0076427 A1 | 3/2009 | Ponsi |
| 2009/0149791 A1 * | 6/2009 | Ponsi .................... A61F 5/0111 |
| | | 602/23 |
| 2009/0227927 A1 | 9/2009 | Frazer |
| 2010/0082060 A1 | 4/2010 | Avitable |
| 2010/0087765 A1 | 4/2010 | Gainey |
| 2010/0152638 A1 | 6/2010 | Ponsi et al. |
| 2010/0312160 A1 | 12/2010 | Creighton et al. |
| 2010/0324517 A1 | 12/2010 | Lenhult et al. |
| 2010/0326442 A1 | 12/2010 | Hamilton |
| 2011/0125183 A1 | 5/2011 | Lipshaw et al. |
| 2011/0180074 A1 | 7/2011 | Gainey |
| 2012/0012118 A1 | 1/2012 | Ponsi et al. |
| 2012/0179082 A1 | 7/2012 | Ponsi et al. |
| 2012/0193957 A1 | 8/2012 | Grover |
| 2012/0209158 A1 | 8/2012 | Avitable et al. |
| 2013/0085427 A1 | 4/2013 | Malhi |
| 2013/0085432 A1 | 4/2013 | Malhi et al. |
| 2013/0123636 A1 | 5/2013 | Longmore |
| 2013/0239976 A1 * | 9/2013 | Purdy ................... A61G 99/00 |
| | | 128/845 |
| 2014/0107547 A1 | 4/2014 | Drey et al. |
| 2014/0173940 A1 | 6/2014 | Drennan |
| 2014/0194796 A1 * | 7/2014 | Noskowicz ............ A61H 9/005 |
| | | 601/151 |
| 2021/0053536 A1 | 2/2021 | Ichiyanagi |

OTHER PUBLICATIONS

"DeRoyal Medical Products PRUventor", "PRUventor Heel Off-loading Device"; Publication Date Unknown but believed to be before the filing date of the present application; http://www.deroyal.com/MedicalProducts.

"Flowtron Universal", Arjo Huntleigh Publication; Flowtron Universal Publication; Published 2009; pp. 1-4.

"Medline Catalog", BioCompression Pneumatic Sleeves by Alimed; Medline Catalog; http://www.medline.com/catalog/catalog.jsp; Unknown Publication date but believed to be prior to present application filing date.

Stanis, Timothy A., "Final Office Action", U.S. Appl. No. 16/859,076, filed Apr. 27, 2020; Mailed Sep. 1, 2022.

Stanis, Timothy A., "Non-Final Office Action", U.S. Appl. No. 16/859,076, filed Apr. 27, 2020; Mailed Dec. 15, 2022.

(56) References Cited

OTHER PUBLICATIONS

Stanis, Timothy, "Non-Final Office Action", U.S. Appl. No. 17/410,237, filed Aug. 24, 2021; Mailed Apr. 28, 2023.
"Medline Catalog", Comfort Lined Sleeve by Ecolab/Microtek; Medline Catalog; http://www.medline.com/catalog/catalog.jsp; Unknown Publication date but believed to be prior to present application filing date.
"Medline Catalog", EHOB Foot Waffle Heel Elevator by Alimed; Medline Catalog; http://www.medline.com/catalog/catalog.jsp; Unknown Publication date but believed to be prior to present application filing date.
"Medline Catalog", Flowtron Compression Garments by Gentinge; Medline Catalog; http://www.medline.com/catalog/catalog.jsp; Unknown Publication date but believed to be prior to present application filing date.
"Medline Catalog", Foot Waffle Air Cushion by Patterson Med; Medline Catalog; http://www.medline.com/catalog/catalog.jsp; Unknown Publication date but believed to be prior to present application filing date.
"Medline Catalog", Foot Waffle Custom by EHOB; Medline Catalog; http://www.medline.com/catalog/catalog.jsp; Unknown Publication date but believed to be prior to present application filing date.
"Medline Catalog", Foot Waffle Heel Elevator Custom by EHOB; Medline Catalog; http://www.medline.com/catalog/catalog.jsp; Unknown Publication date but believed to be prior to present application filing date.
"Medline Catalog", Kendall SCD Compression System by Medtronic; Medline Catalog; http://www.medline.com/catalog/catalog.jsp; Unknown Publication date but believed to be prior to present application filing date.
"Medline Catalog", Leg Compression Garments by Currie Medical; Medline Catalog; http://www.medline.com/catalog/catalog.jsp; Unknown Publication date but believed to be prior to present application filing date.
"Medline Catalog", Prevalon Heel Protectors by Sage Products; Medline Catalog; http://www.medline.com/catalog/catalog.jsp; Unknown Publication date but believed to be prior to present application filing date.
"Medline Catalog", Rolyan Neoprene Elbow Sleeve By Patters; Medline Catalog; http://www.medline.com/catalog/catalog.jsp; Unknown Publication date but believed to be prior to present application filing date.
"Medline Catalog", SCD Express Compression System by Covidien; Medline Catalog; http://www.medline.com/catalog/catalog.jsp; Unknown Publication date but believed to be prior to present application filing date.
"Medline Catalog", SCD Express Sleeve (Knee Length) by Stryker; Medline Catalog; http://www.medline.com/catalog/catalog.jsp; Unknown Publication date but believed to be prior to present application filing date.
"Medline Catalog", SCD Express Thigh Length Sleeves by Covidien; Medline Catalog; http://www.medline.com/catalog/catalog.jsp; Unknown Publication date but believed to be prior to present application filing date.
"Medline Catalog", VasoGrad Dvt Sleeves by Compression Therapy Concepts; Medline Catalog; http://www.medline.com/catalog/catalog.jsp; Unknown Publication date but believed to be prior to present application filing date.
"Medline Catalog", Waffle FootHold Splint with Anti-Rotation; Medline Catalog; http://www.medline.com/catalog/catalog.jsp; Unknown Publication date but believed to be prior to present application filing date.
"Medline Catalog", Waffle FootHold with Secure stick Sole by EHOB; Medline Catalog; http://www.medline.com/catalog/catalog.jsp; Unknown Publication date but believed to be prior to present application filing dat.
"Medline Catalog", WAFFLE FootHold with Splint by EHOB; Medline Catalog; http://www.medline.com/catalog/catalog.jsp; Unknown Publication date but believed to be prior to present application filing date.
"Medline Catalog", WAFFLE Heel Elevator by EHOB; Medline Catalog; http://www.medline.com/catalog/catalog.jsp; Unknown Publication date but believed to be prior to present application filing date.
"Medline Catalog", Waffle Heel Protectors by EHOB; Medline Catalog; http://www.medline.com/catalog/catalog.jsp; Unknown Publication date but believed to be prior to present application filing date.
"Website", Covidien Vascular Compression Products; www.covidien.com/vascularcompression/pages.aspx; Publicly available prior to filing of this application.
Han, Inho, "PCT Search Report and Written Opinion", PCT/US2013/063852, filed Oct. 8, 2013; Mailed Jan. 8, 2014.
Han, Inho, "PCT Search Report and Written Opinion", PCT/US2014/026259, filed Mar. 13, 2014; Mailed Jul. 7, 2014.
Krakower, Susan, "Final OA", U.S. Appl. No. 29/473,963, filed Nov. 27, 2013; Mailed Jul. 7, 2014.
Krakower, Susan, "NonFinal OA", U.S. Appl. No. 29/473,963, filed Nov. 27, 2013; Mailed Jan. 24, 2014.
Krakower, Susan, "Notice of Allowance", U.S. Appl. No. 29/444,693, filed Feb. 1, 2013; Mailed Aug. 27, 2013.
Krawkower, Susan, "Notice of Allowance", U.S. Appl. No. 29/473,963, filed Nov. 27, 2013; Mailed Oct. 20, 2015.
Kroakower, Susan, "Ex Parte Quayle", U.S. Appl. No. 29/473,963, filed Nov. 27, 2013; mailed Feb. 20, 2015.
Patel, Tarla, "NonFinal Office Action", U.S. Appl. No. 14/468,872, filed Aug. 26, 2014; Mailed Aug. 8, 2017.
Patel, Tarla, "Notice of Allowance", U.S. Appl. No. 15/892,186, filed Feb. 8, 2018; Mailed Aug. 26, 2020.
Shin, Ju C., "PCT Search Report and Written Opinion", PCT/US2014/013780, file Jan. 30, 2014; Mailed May 19, 2014.
Stanis, Timothy, "Final OA", U.S. Appl. No. 13/649,920, filed Oct. 11, 2012; Mailed Jun. 2, 2016.
Stanis, Timothy, "Final OA", U.S. Appl. No. 13/757,233, filed Feb. 1, 2013; Mailed Apr. 18, 2016.
Stanis, Timothy, "Final OA", U.S. Appl. No. 14/206,395, filed Mar. 12, 2014; Mailed Nov. 21, 2016.
Stanis, Timothy, "NonFinal OA", U.S. Appl. No. 13/649,920, filed Oct. 11, 2012; Mailed Dec. 2, 2015.
Stanis, Timothy, "NonFinal OA", U.S. Appl. No. 13/757,233, filed Feb. 1, 2013; Mailed Oct. 2, 2015.
Stanis, Timothy, "NonFinal OA", U.S. Appl. No. 14/206,395, filed Mar. 12, 2014; Mailed May 16, 2016.
Stanis, Timothy, "NonFinal OA", U.S. Appl. No. 15/260,918, filed Sep. 9, 2016; Mailed Sep. 14, 2018.
Stanis, Timothy, "NonFinal OA", U.S. Appl. No. 15/677,958, filed Aug. 15, 2017; Mailed Oct. 2, 2019.
Stanis, Timothy, "Notice of Allowance", U.S. Appl. No. 13/649,920, filed Oct. 11, 2012; Mailed Jan. 13, 2016.
Stanis, Timothy, "NonFinal Office Action", U.S. Appl. No. 16/278,318, filed Apr. 8, 2019; Mailed Jul. 20, 2021.
Stanis, Timothy, "NonFinal Office Action", U.S. Appl. No. 16/859,076, filed Apr. 27, 2020; Mailed Feb. 28, 2022.
Stanis, Timothy, "Notice of Allowance", U.S. Appl. No. 13/649,920, filed Oct. 11, 2012; Mailed Oct. 6, 2016.
Stanis, Timothy, "Notice of Allowance", U.S. Appl. No. 13/757,233, filed Feb. 1, 2013; Mailed Jun. 22, 2016.
Stanis, Timothy, "Notice of Allowance", U.S. Appl. No. 14/206,395, filed Mar. 12, 2014; Mailed May 18, 2017.
Stanis, Timothy, "Notice of Allowance", U.S. Appl. No. 15/260,918, filed Sep. 9, 2016; Mailed Jan. 7, 2019.
Watkins, Jennifer, "Final OA", U.S. Appl. No. 29/500,542, filed Aug. 26, 2014; Mailed Jun. 28, 2016.
Watkins, Jennifer, "NonFinal OA", U.S. Appl. No. 29/500,542, filed Aug. 26, 2014; Mailed Mar. 8, 2016.
Watkins, Jennifer, "Notice of Allowance", U.S. Appl. No. 29/500,542, filed Aug. 26, 2014; Mailed Nov. 2, 2016.

* cited by examiner

HEEL PROTECTOR AND CORRESPONDING REHABILITATION SYSTEMS AND METHODS FOR USING THE SAME

CROSS REFERENCE TO PRIOR APPLICATIONS

This application is a continuation application claiming priority under 35 USC § 120 from U.S. application Ser. No. 16/993,737, filed Aug. 14, 2020, which is a divisional application claiming priority under 35 USC § 121 from U.S. application Ser. No. 15/892,186, filed Feb. 8, 2018, which is a continuation application claiming priority under 35 USC § 120 to U.S. application Ser. No. 14/468,872, filed Aug. 26, 2014, each of which is incorporated by reference for all purposes.

BACKGROUND

Technical Field

This disclosure relates generally to ulcer prevention, and more particularly to devices for preventing ulcer complications during therapy.

Background Art

Limb protection devices, including boots, braces, wraps, socks, sleeves, and the like are used to protect a patient's limbs. These devices can be used for a variety of reasons, including limb elevation, limb pressure alleviation, limb protection, and limb strengthening.

While many of these devices work reasonably well in practice, problems with their usage exist. When used incorrectly, these devices can sometimes lead to skin breakdown or the formation of pressure ulcers. For example, if a patient's limb rolls to an incorrect position while wearing a protection device, the device itself can create new medical conditions that must be treated while aiding in the rehabilitation of previously existing conditions. These new issues only serve to extend the overall rehabilitation time for the patient. Accordingly, it would be advantageous to have an improved therapeutic device.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present disclosure.

Figure 1:
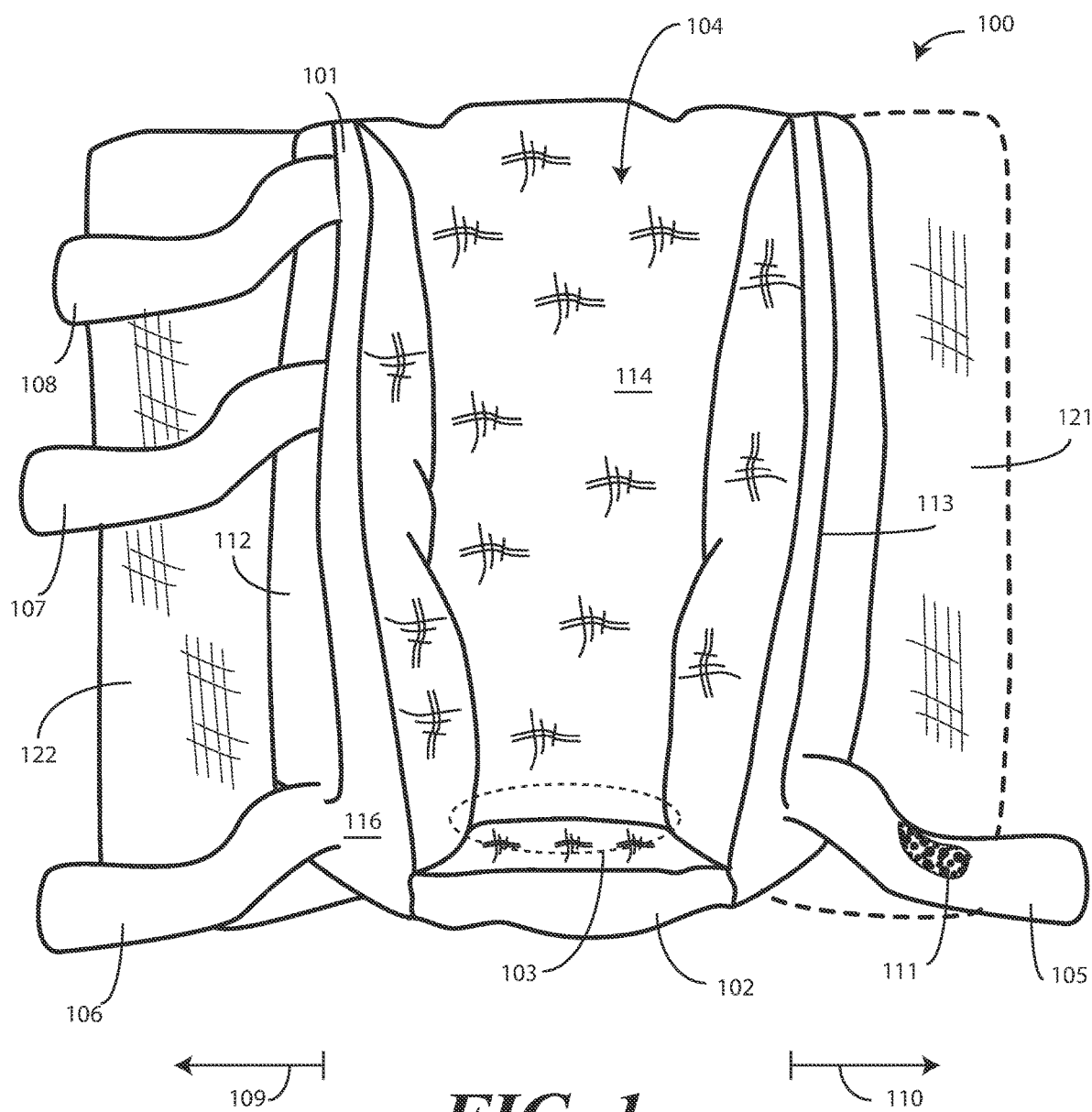
FIG. 1 illustrates a front elevation view of one explanatory device in accordance with one or more embodiments of the disclosure.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present disclosure.

DETAILED DESCRIPTION OF THE DRAWINGS

Embodiments of the disclosure are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing FIG. A would refer to an element, 10, shown in figure other than FIG. A.

Embodiments of the present disclosure provide a cushioned device that is configured for providing protection to a person's leg, foot, or heel during treatment or rehabilitation. In one embodiment, a device includes a leg engaging section and a foot engaging section. The leg engaging section and the foot engaging section intersect at a heel receiver. In one embodiment, the leg engaging section and the foot engaging section define a leg insertion aperture into which a patient's leg map be placed. To provide protection for the patient's leg during treatment or rehabilitation, in one embodiment the leg engaging section includes a compressible cushion layer. The compressible cushion layer can be an organic batting, such as a cotton or wool batting, or may alternatively be an inorganic batting, such as a poly fiber fill, compressible foam, or a synthetic material. Of course, combinations of organic batting materials and inorganic batting materials may also be used.

In one embodiment, the device includes at least one bolster tube. Advantageously, in one embodiment the bolster tube is integrated into the leg engaging section. For example, the bolster tube can be disposed interior the leg engaging section such that it is surrounded, or at least partially surrounded, by the compressible cushion layer of the leg engaging section. In another embodiment, the bolster tube is selectively removable from the leg engaging section. For example, in one embodiment the leg engaging section includes one or more pockets into which the bolster tube may be inserted. Advantageously, integrating the bolster tube into the leg engaging section ensures proper use and positioning of the bolster tube to avoid inadvertent rolling or twisting of a patient's leg while in the device. This helps to preclude the aforementioned maladies of skin breakdown or pressure ulcers that result from misapplication of prior art heel protection boots.

In one embodiment, one bolster tube is incorporated into the leg engaging section. For example, the single bolster tube can be incorporated into one side of the leg insertion aperture such that it is disposed to the outside of a patient's tibia when the patient's leg is positioned within the device. In another embodiment, two bolster tubes can be integrated into the leg engaging sections to prevent inadvertent rolling of the leg in either the clockwise or counterclockwise directions.

Embodiments of the disclosure contemplate that patients have a tendency to roll their feet outward, i.e., away from each other, when lying on their backs in a bed. Embodiments of the disclosure also contemplate that prior art heel protection devices tend to exacerbate this rotational tendency. When the foot or leg rotates while a prior art protection device is being worn, the protection device can become dislodged. Additionally, the patient's heel may become mis-located within the protection device.

Prior art attempts to prevent rotation include placing a pillow, stabilization wedge, or other support device against the heel protector. However, embodiments of the disclosure contemplate that such devices tend to move away from the heel protector, fall off the bed, or become misplaced on the bed.

To rectify this problem, embodiments of the disclosure advantageously incorporate a stabilizing bar, referred to as a bolster tube herein, between the inner and outer material of the leg engaging section. In one embodiment, the bolster tube is manufactured from foam, and helps to keep the device supported without the need of external stabilization devices such as pillow or stabilization wedge. In one or more embodiments, the bolster tubes are selectively removable such that they can be inserted into, and removed from, the inner and outer fabric of the leg engaging section. In one or more embodiments, the bolster tubes can be manufactured in different sizes so that different amounts of stability can be provided by inserting different sized bolster tubes.

In one or more embodiments, the bolster tubes are integrated into the device to provide resistance to rotational motion of the patient's leg when the device is being worn. Said differently, the bolster tubes are integrated into the device to stabilize the device rotationally when worn by a patient. The bolster tubes can take different shapes. In one embodiment, the bolster tube is generally triangular in cross section. Where the device is configured to allow insertion and removal of the bolster tube, the triangular cross section offers "ambidextrous" stabilization in that it can be inserted into either side of the leg engaging section. While a triangular cross section of the bolster tube is one possible shape, other cross sectional shapes such as polygons, ovals, circles, and the like will be obvious to those of ordinary skill in the art having the benefit of this disclosure.

In one embodiment, the leg engaging section intersects with the foot engaging section and a heel receiver. A leg insertion aperture is defined along the leg engaging section and a foot engaging section. Once the patient's limb is placed within the leg insertion aperture, one or more fastening straps can wrap from one side of the leg engaging portion across the leg insertion aperture to another side of the leg engaging portion to retain the overall device on the patient's limb.

Figure 2:
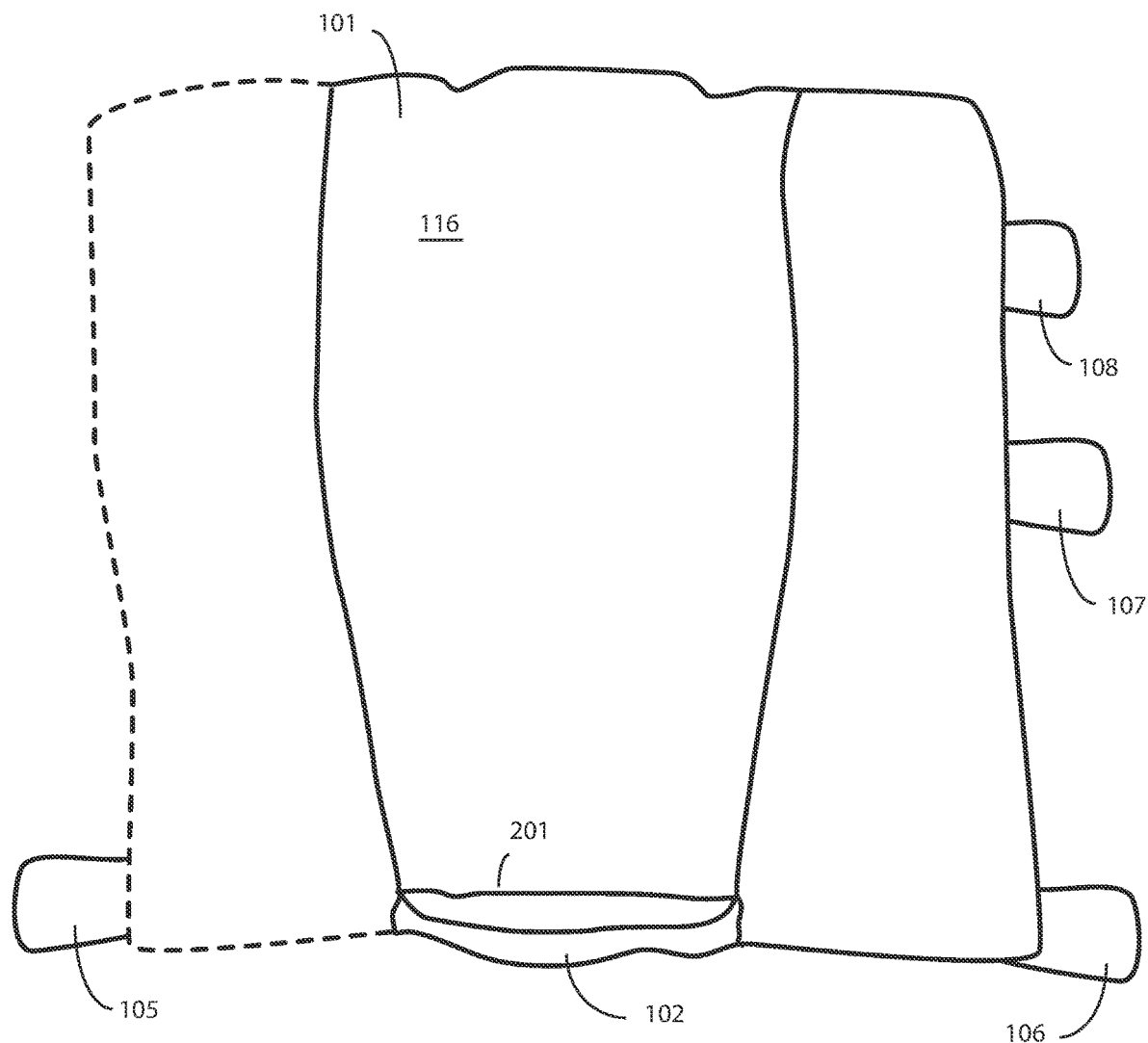
FIG. 2 illustrates a rear elevation view of one explanatory device in accordance with one or more embodiments of the disclosure.
Figure 3:
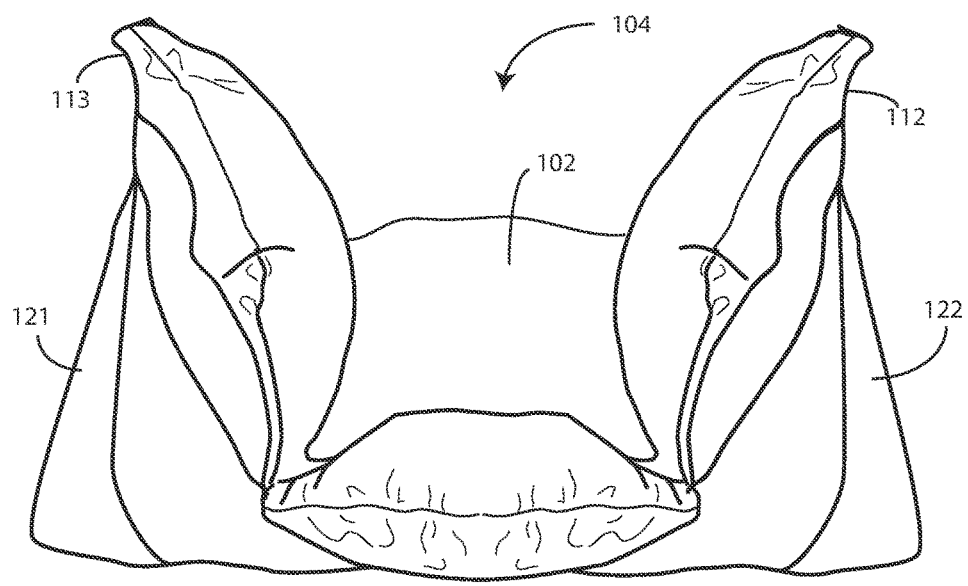
FIG. 3 illustrates a top plan view of one explanatory device in accordance with one or more embodiments of the disclosure.

Turning now to FIGS. 1-3, illustrated therein is one explanatory device 100 in accordance with one or more embodiments of the disclosure. In the illustrative embodiment of FIGS. 1-3, the device 100 includes a leg engaging section 101 and a foot engaging section 102. The leg engaging section 101 intersects the foot engaging section 102 at a heel receiver 103. In one embodiment, the heel receiver 103 defines an aperture 201 through which a patient's heel can be seen when the device 100 is applied to the patient's leg. In other embodiments, the aperture 201 is omitted. The leg engaging section 101 and the foot engaging section 102 have defined therealong a leg insertion aperture 104. A patient's leg can be inserted through the leg insertion aperture 104, as will be shown in FIG. 8 below.

In one embodiment, the device 100 can include one or more fastening straps 105,106,107,108 extending from the sides of the leg engaging section 101, the foot engaging section, or combinations thereof. For example, in the illustrative embodiment of FIGS. 1 and 2, the device 100 has four fastening straps 105,106,107,108 extending from its sides. At least one fastening strap 105 extends from a first side of the device 100, while others extend from another side of the device 100. This allows the fastening straps to "criss-cross" from one side of the device 100 to the other. In this illustrative embodiment, two fastening straps 105,106 extend from the foot engaging section 102, while two other fastening straps 107,108 extend from the leg engaging section 101. Also, in this illustrative embodiment, three fastening straps 106,107,108 extend from the medial side 109 of the device 100, while one fastening strap 105 extends from the lateral side 110 of the device 100. This configuration is illustrative only, as other configurations and placements of the fastening straps 105,106,107,108 will be obvious to those of ordinary skill in the art having the benefit of this disclosure.

In one embodiment, the fastening straps 105,106,107,108 are stretchable. For example, they may comprise an elasticized material configured to stretch when being wrapped about the leg insertion aperture 104. In another embodiment, the fastening straps 105,106,107,108 are not stretchable, but are rather material layers that are fixed in length and do not change when being wrapped about the leg insertion aperture 104. The fastening straps 105,106,107,108 are affixed to the device 100 by stitching in one embodiment. FIG. 2 illustrates fastening straps 107,108 being attached to the leg engaging section 101 along seam 202.

In one embodiment, each of the fastening straps 105,106, 107,108 comprises one of a hook fastener or a loop fastener disposed therealong. Illustrating by example, fastening strap 105 may have hook fasteners disposed along side 111. To complete the fastening system, in one embodiment the leg engaging section 101 includes one or more panels 112,113 that have a complementary fastener disposed therealong. Where, for example, fastening strap 105 includes hook fasteners, corresponding panel 112 may have loop fasteners disposed therealong, as the loop fasteners are complementary to the hook fasteners. Accordingly, when fastening strap 105 is wrapped across the leg insertion aperture 104, it can be attached anywhere along panel 112. The same is true with fastening straps 106,107,108 attaching to panel 113. While hook and loop fasteners are one type of fastener or attachment mechanism suitable for use with embodiments of the disclosure, it should be noted that others will be obvious to those having ordinary skill in the art and the benefit of this disclosure. For example, the hook and loop fasteners can be replaced by laces, snaps, buttons, drawstrings, or other fastening devices.

In one embodiment, the interior lining 114 of the central portion of the leg engaging section 101 is soft and comfortable. For example, in one embodiment the interior lining 114 can be fleece or another soft material. In another embodiment, the interior lining 114 can be felt or chamois. Other soft and comfortable materials will be obvious to those of ordinary skill in the art having the benefit of this disclosure.

In one embodiment, the interior lining 114 has a relatively high coefficient of friction so that the device 100 does not move when wrapped about a patient's limb or compression device attached thereto. For example, the interior lining 114 can be brushed, napped or sanded to raise its pile for comfort and increase the coefficient of friction. In one embodiment, the interior lining 114 has an antibacterial, antimicrobial, or anti-odor material integrated therein to help reduce the risk of bacteria, microbes, or odors from existing in the interior of the device 100 after prolonged use. The interior lining 114 can also be manufactured from a wicking material. The exterior 116 of the device 100 may be water resistant or waterproof as desired. In one embodiment, the interior of the device 100 can be constructed from a cooling material, such as a gel that can be cooled to apply thermal therapy to the patient.

In one embodiment, the leg engaging section 101 includes two side members 121,122. As will be shown in more detail below with reference to FIGS. 4-6, in one embodiment one or more bolster tubes are placed interior to the leg engaging section 101 along the side members 121,122. Advantageously, the side members 121,122 can extend outwardly to increase the overall width of the leg engaging section 101. However, in one or more embodiments the one or more bolster tubes can be placed interior the leg engaging sections regardless of to what width the side members 121,122 extend.

Figure 4:
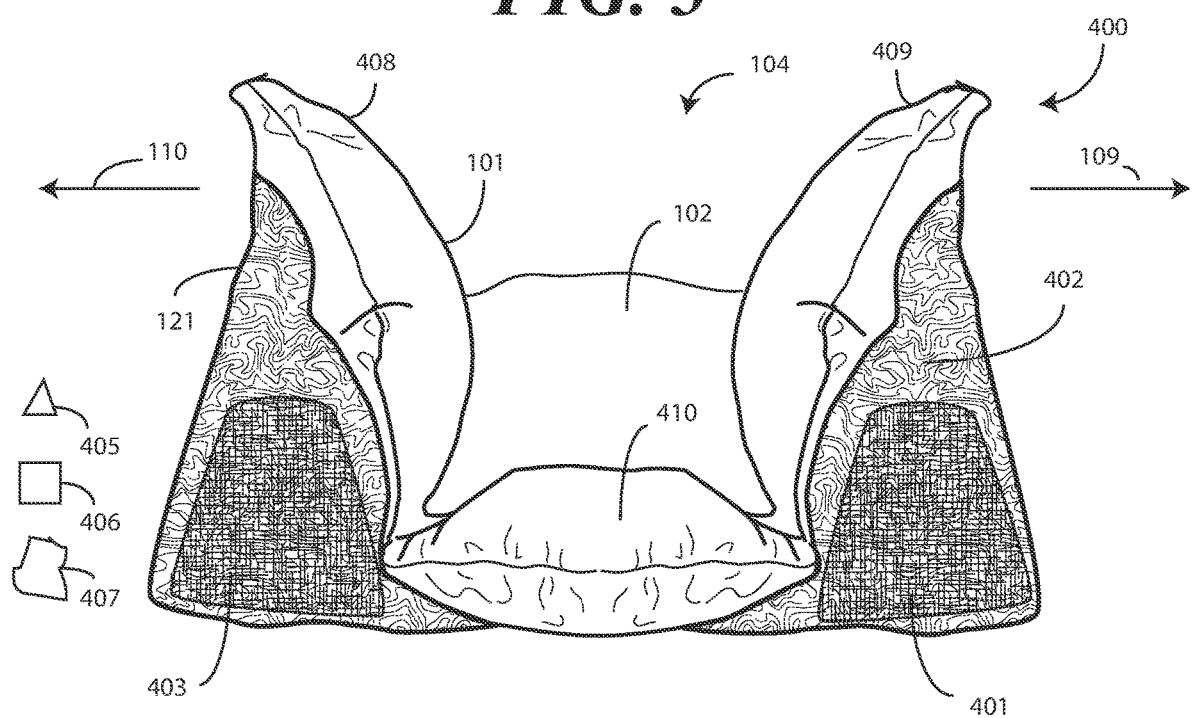
FIG. 4 illustrates a sectional view of one explanatory device in accordance with one or more embodiments of the disclosure.

Turning now to FIG. 4, illustrated therein is one embodiment of a device 400 in accordance with one or more embodiments of the disclosure. The device 400 is shown in FIG. 4 sectional view so that internal and external components can be seen.

In this illustrative embodiment, the device 400 includes a leg engaging section 101 and a foot engaging section 102 intersecting at a heel receiver. The leg engaging section 101 and the foot engaging section 102 define a leg insertion aperture 104. At least the leg engaging section includes a compressible cushion layer 402. The compressible cushion layer 902 can be manufactured from one of an organic batting or an inorganic batting, or alternatively of combinations thereof.

As shown in FIG. 4, at least one bolster tube 401 is disposed interior to the leg engaging section 101. In one embodiment, the bolster tube 401 is manufactured from compressible foam. However, other materials can be used as well. For example, in another embodiment the bolster tube 401 is manufactured from an organic batting. In another embodiment, the bolster tube 401 is manufactured from an inorganic batting. In yet another embodiment, the bolster tube 401 is inflatable and can be selectively inflated or deflated as needed by a user. Other materials suitable for the bolster tube will be obvious to those of ordinary skill in the art having the benefit of this disclosure.

In this embodiment, a first bolster tube 401 and a second bolster tube 403 are disposed interior to the leg engaging section 101 along the side members 121,122. In this embodiment, the first bolster tube 401 and the second bolster tube 403 are at least partially surrounded by the compressible cushion layer 902. In this embodiment, the first bolster tube 401 and the second bolster tube 403 are completely surrounded by the compressible cushion layer.

In one embodiment, the first bolster tube 401 is disposed along a first side of the leg engaging section 101, while the second bolster tube 403 is disposed along a second side of the leg engaging section 101. In one embodiment, the first side and the second side are on opposite sides of the device 400. Illustrating by example, as shown in FIG. 4, the first bolster tube 401 is disposed along the medial side 109 of the device 400, while the second bolster tube 403 is disposed along the lateral side 110 of the device 400. The use of two bolster tubes on opposite sides of the device 400 provides rotational stability in both the clockwise and counterclockwise directions.

In this illustrative embodiment, the first bolster tube 401 and the second bolster tube 403 are trapezoidal in cross section. However, it can take other shapes as well. For example the first bolster tube 401 and the second bolster tube 403 can be triangular 405 in cross section, square 406 in cross section, or take a free-form 407 cross section. Still other shapes will be obvious to those of ordinary skill in the art having the benefit of this disclosure.

In this embodiment, the first bolster tube 401 and the second bolster tube 403 work to provide resistance to rotational motion of the patient's leg. Said differently, the first bolster tube 401 and the second bolster tube 403 are configured to stabilize the device 400 rotationally when worn by a patient. In this illustrative embodiment, the first bolster tube 401 and the second bolster tube 403 provide an "ambidextrous" stabilization by being placed on either side of the device 400. As will be shown below with reference to FIG. 6, in other embodiments a single bolster tube can be used.

In the illustrative embodiment of FIG. 4, the first bolster tube 401, the second bolster tube 403, and the leg engaging section 101 are arranged in a substantially parallel alignment. As shown in FIG. 4, each of the first bolster tube 401, the second bolster tube 403 and the leg engaging section 101 extend along lines running substantially orthogonally into the page, which makes each element substantially parallel.

In the illustrative embodiment of FIG. 4, the leg engaging section 101 defines a first side 408, a second side 409, and a base member 410 disposed between the first side 408 and the second side 410. In this illustrative embodiment, the first bolster tube 401 is disposed exterior, i.e., to the left as viewed in FIG. 4, of the first side 408. Similarly, in this embodiment the second bolster tube 403 is disposed exterior, i.e., to the right as viewed in FIG. 4, of the second side 409. This positioning places each first bolster tube 401 and the second bolster tube 403 exterior of the patient's leg when the device 400 is worn.

Figure 5:
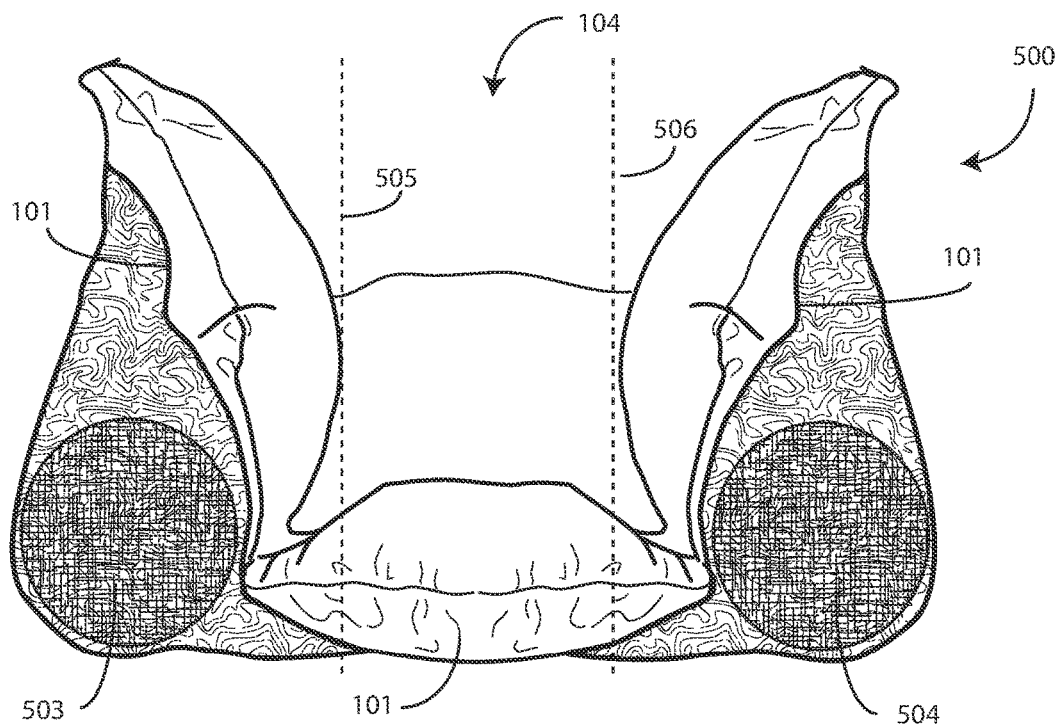
FIG. 5 illustrates a sectional view of another explanatory device in accordance with one or more embodiments of the disclosure.

Turning now to FIG. 5, illustrated therein is an alternate device 500 configured in accordance with one or more embodiments of the disclosure. To provide additional lateral stability, the device 500 of FIG. 5 includes two foam or air-filled bolster tubes 501,503 disposed within the leg engaging section 101 exterior to the leg receiving aperture 104. The bolster tubes 501,503 of FIG. 5 are circular in cross section. However, they can take other shapes, including polygonal shapes, as noted above. The compressible cushion layer 502 at least partially surrounds the first bolster tube 501 and the second bolster tube 502 in this embodiment. As noted above, the compressible cushion layer 502 can comprise one of an organic batting, an inorganic batting, or combinations thereof.

In this illustrative embodiment, the first tube 501 disposed to a first side of a leg insertion aperture sideline 505 of the leg engaging section 101, while the second bolster tube 503 is disposed to a second side of a second leg insertion aperture sideline 506 disposed opposite the leg insertion aperture 104 from the first leg insertion aperture sideline 505. When a patient's limb is inserted into the leg insertion aperture 104, placement of the limb on the leg engaging section 101 causes the first tube 1201 and the second tube 1202 to be disposed to either side of the patient's limb, thereby increasing stability.

Figure 6:
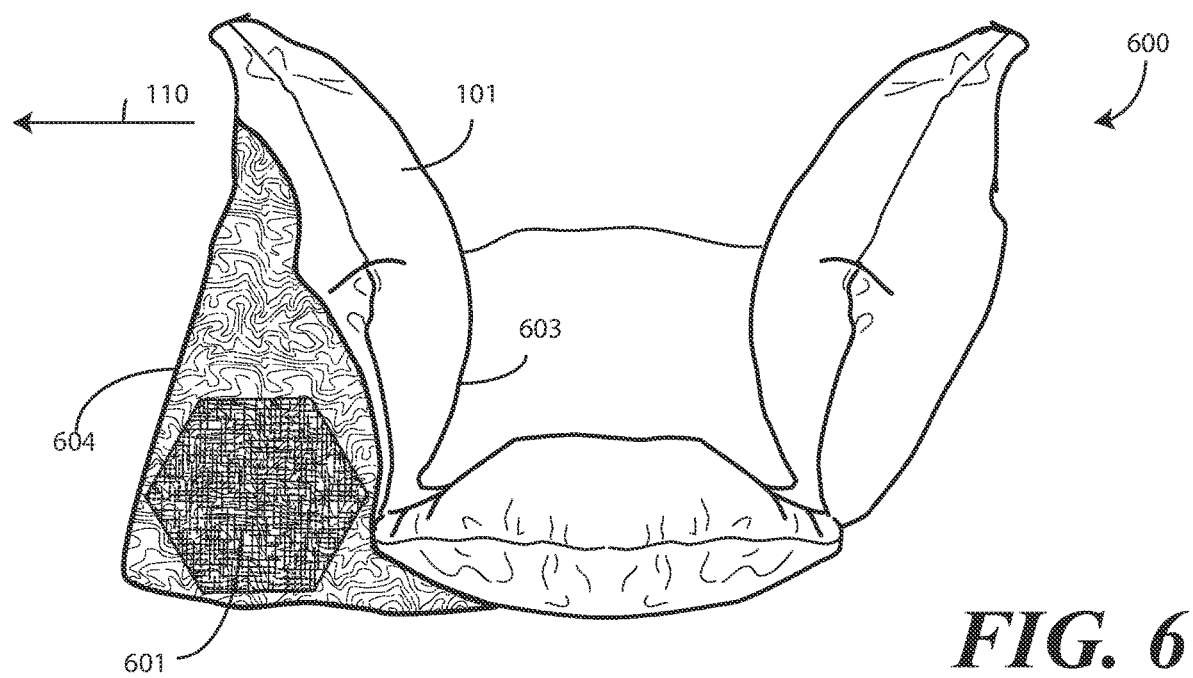
FIG. 6 illustrates a sectional view of another explanatory device in accordance with one or more embodiments of the disclosure.

Turning now to FIG. 6, illustrated therein is a device 600 that includes only one bolster tube 601. This bolster tube 601 is polygonal in cross section, and is placed on the lateral side 110 of the device 600. Accordingly, when worn on a patient's left leg, the bolster tube 601 would be placed on the lateral side of the leg. If the device 600 was to be placed on the right leg, and a single bolster tube 601 was used, in one embodiment the cross sectional view would be the mirror image of that shown in FIG. 6. In this illustrative embodiment, the bolster tube 601 is completely surrounded by the compressible cushion layer 402.

Figure 7:
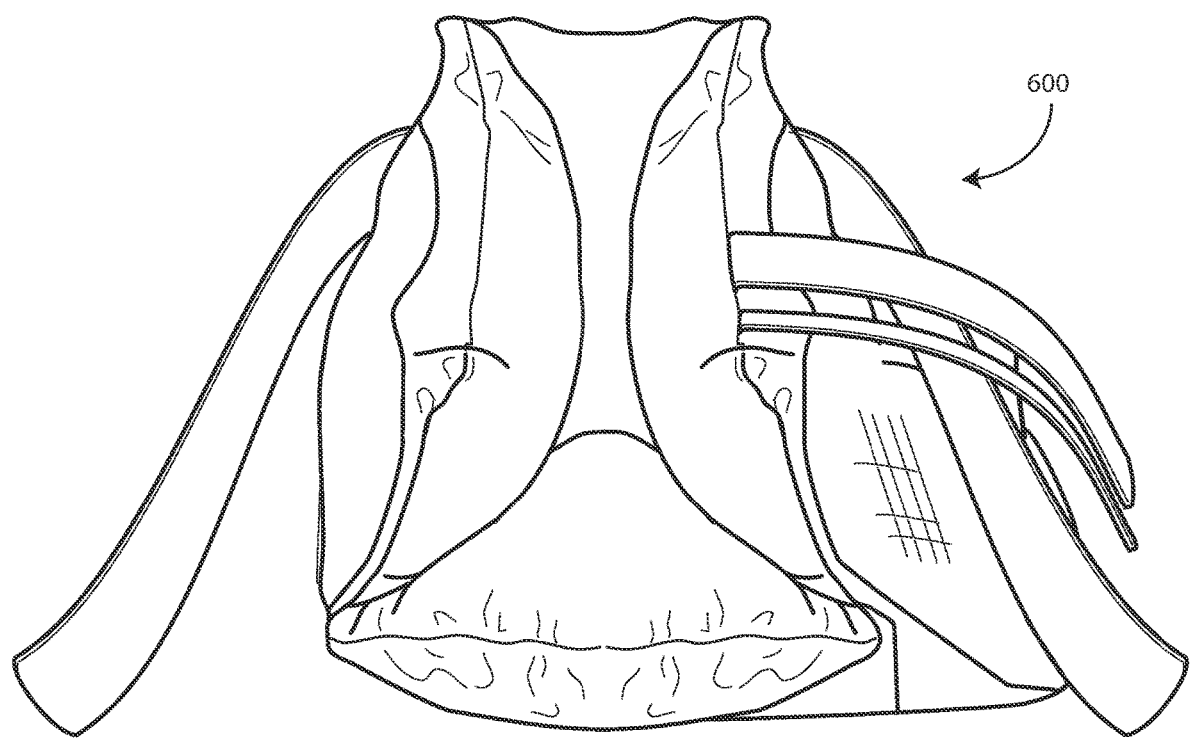
FIG. 7 illustrates a front elevation view of one explanatory device in accordance with one or more embodiments of the disclosure.

In this embodiment, as was the case in the embodiments of FIGS. 3-5, the bolster tube 601 is disposed between the inner material 603 and the outer material 604 of the leg engaging section 101. In one embodiment, the bolster tube 601 is manufactured from foam, and helps to keep the device 600 supported without the need of external stabilization devices such as pillow or stabilization wedge. A front elevation view of the device 600 of FIG. 6 is shown in FIG. 7

Figure 8:
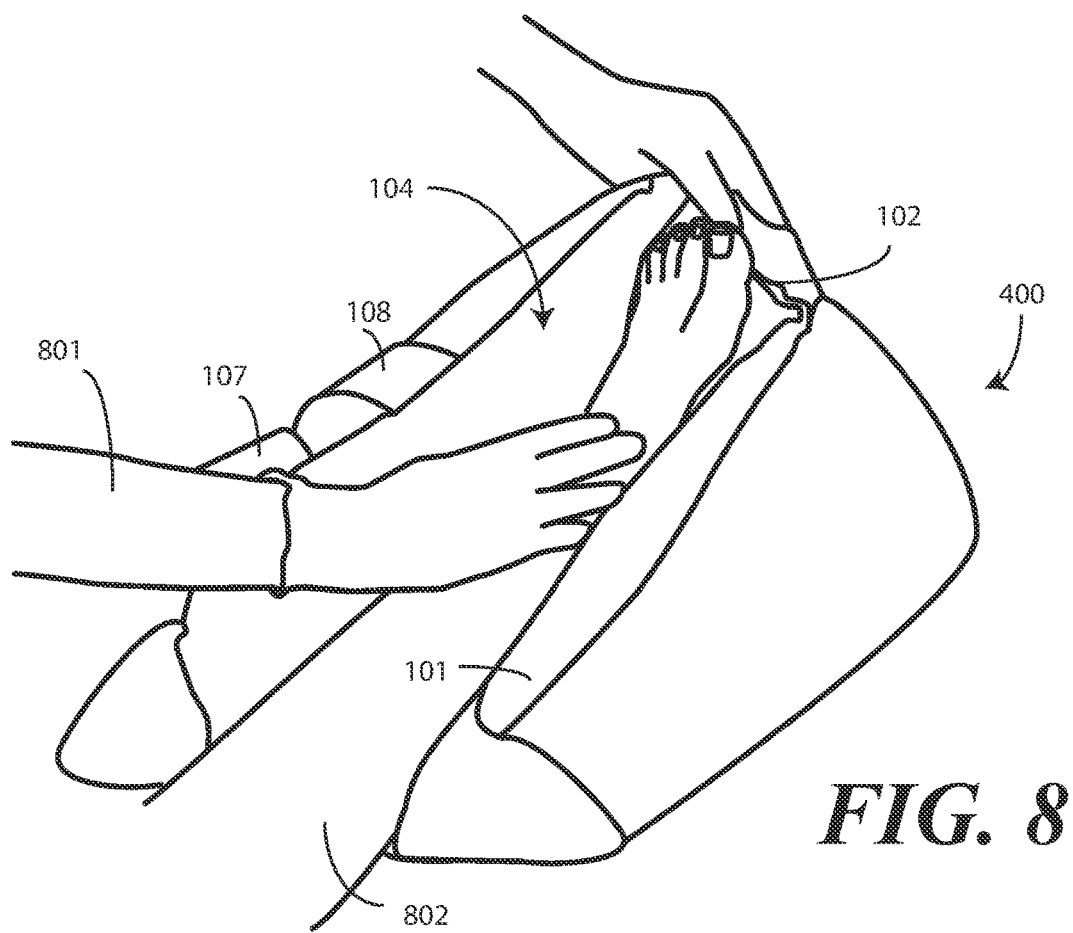
FIG. 8 illustrates an explanatory step of a method of using an explanatory device in accordance with one or more embodiments of the disclosure.
Figure 9:
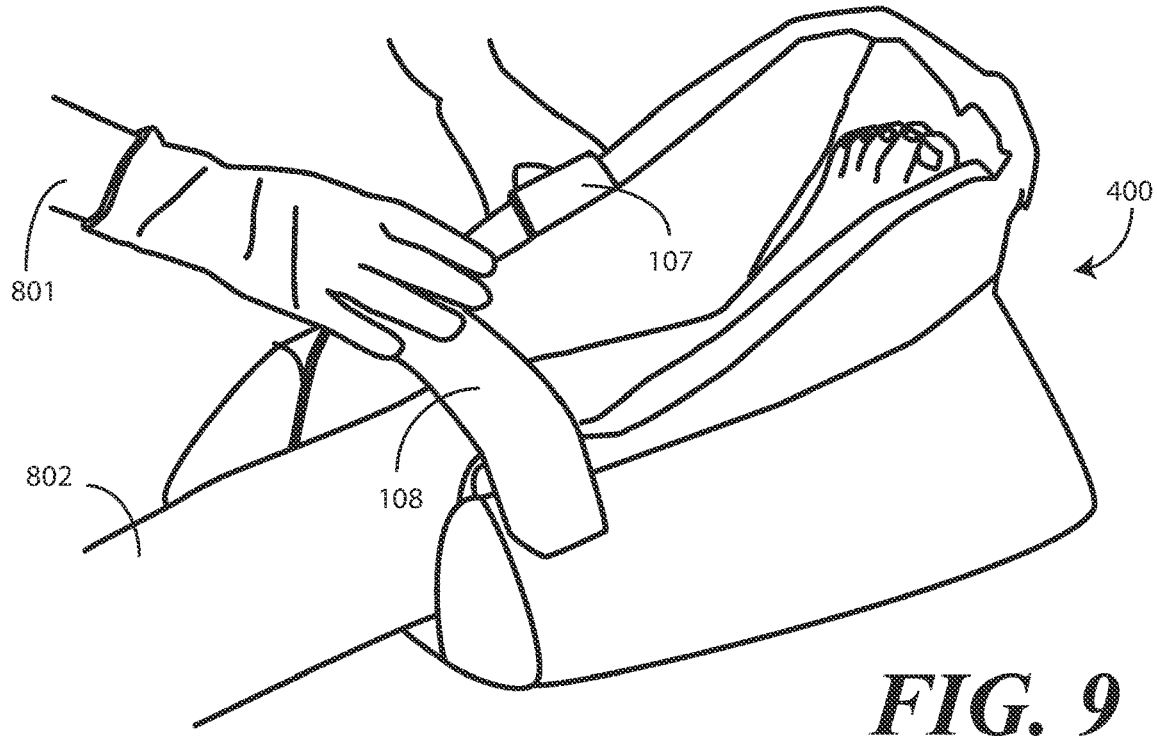
FIG. 9 illustrates another explanatory step of a method of using an explanatory device in accordance with one or more embodiments of the disclosure.
Figure 10:
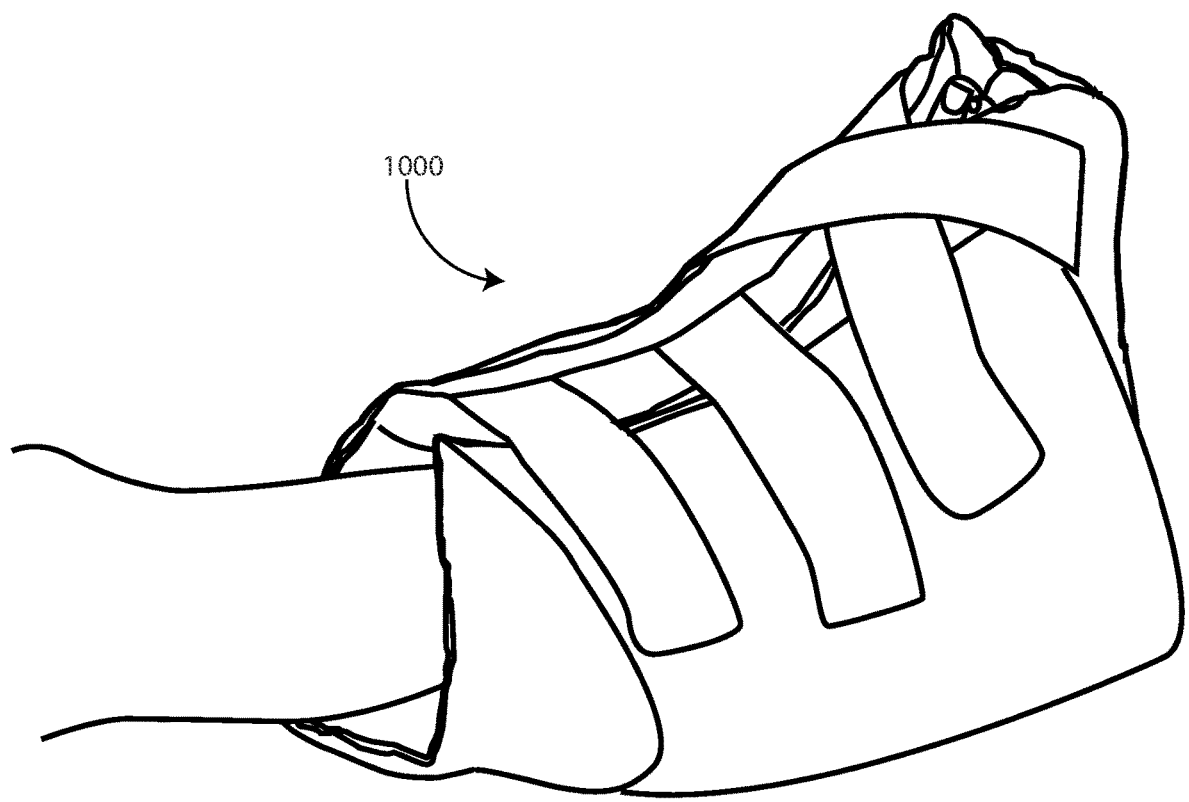
FIG. 10 illustrates an explanatory device in accordance with one or more embodiments of the disclosure in use.

Turning now to FIGS. 8-10, a method of applying a device 400 is illustrated. While the device 400 is که of the embodiment of FIG. 4, the same method could be used with any of the devices described above. As shown in FIG. 8, a health care services provider 801 passes a patient's leg 802 through the leg insertion aperture 104 disposed along the leg engaging section 101 and the foot engaging section 102 such that the patient's heel engages the heel receiver (103). Once this step is complete, the health care services provider 801 will wrap the fastening straps 107,108 across the leg insertion aperture 104 to retain the device 400 to the patient's leg 302 as shown in FIG. 9. The result 1000 of this wrapping is shown in FIG. 10.

Figure 11:
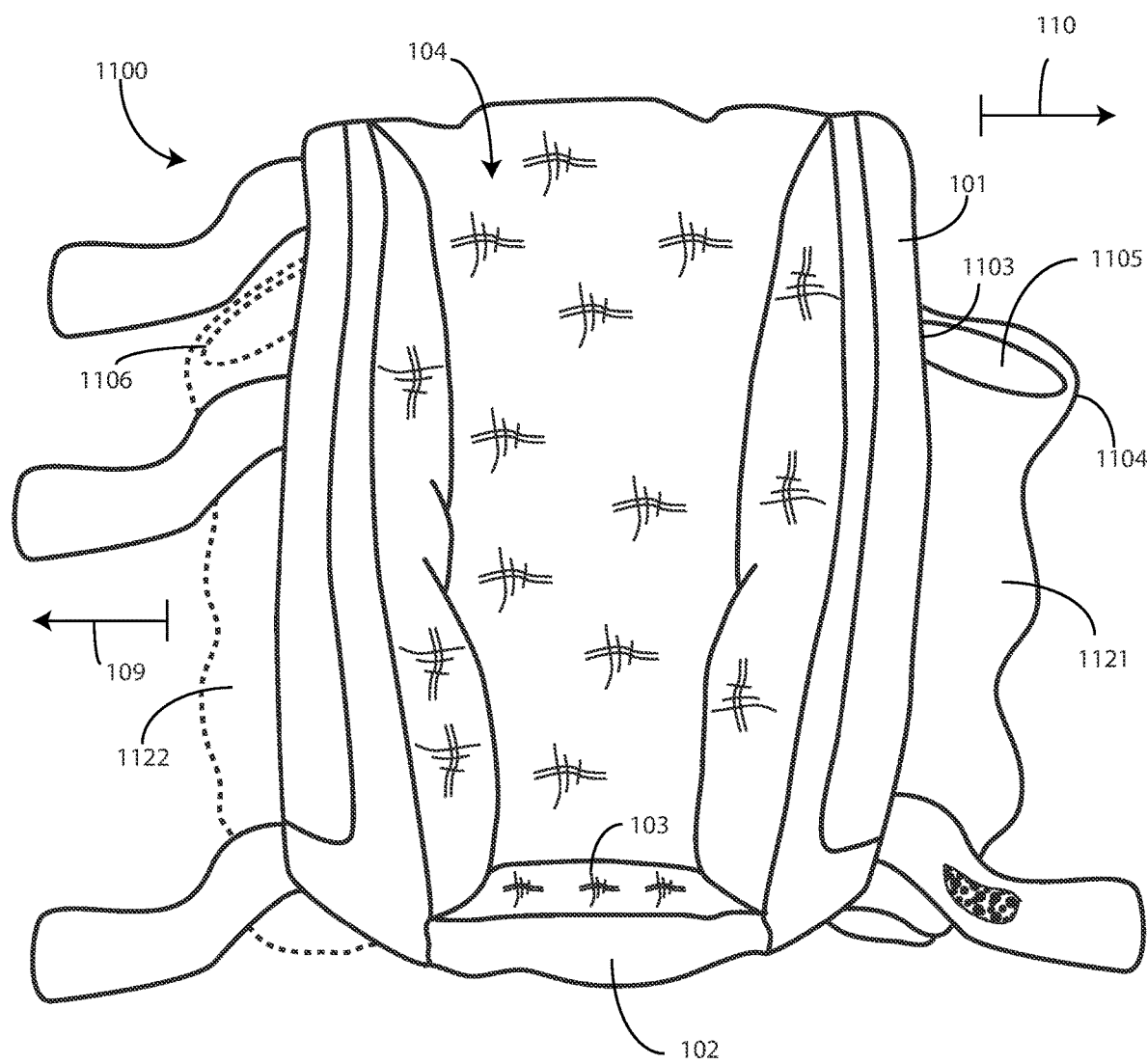
FIG. 11 illustrates a front elevation view of another explanatory device in accordance with one or more embodiments of the disclosure.

Turning now to FIG. 11, illustrated therein is yet another device 1100 configured in accordance with one or more embodiments of the disclosure. As with the device (100) of FIG. 1, the device 1100 of FIG. 11 includes a leg engaging section 101 and a foot engaging section 102. The leg engaging section 101 intersects the foot engaging section 102 at a heel receiver 103. The heel receiver 103 can optionally define an aperture through which a patient's heel can be seen when the device 1100 is applied to the patient's leg. The leg engaging section 101 and the foot engaging section 102 have defined a leg insertion aperture 104 through which a patient's leg can be inserted into the device 1100.

Figure 12:
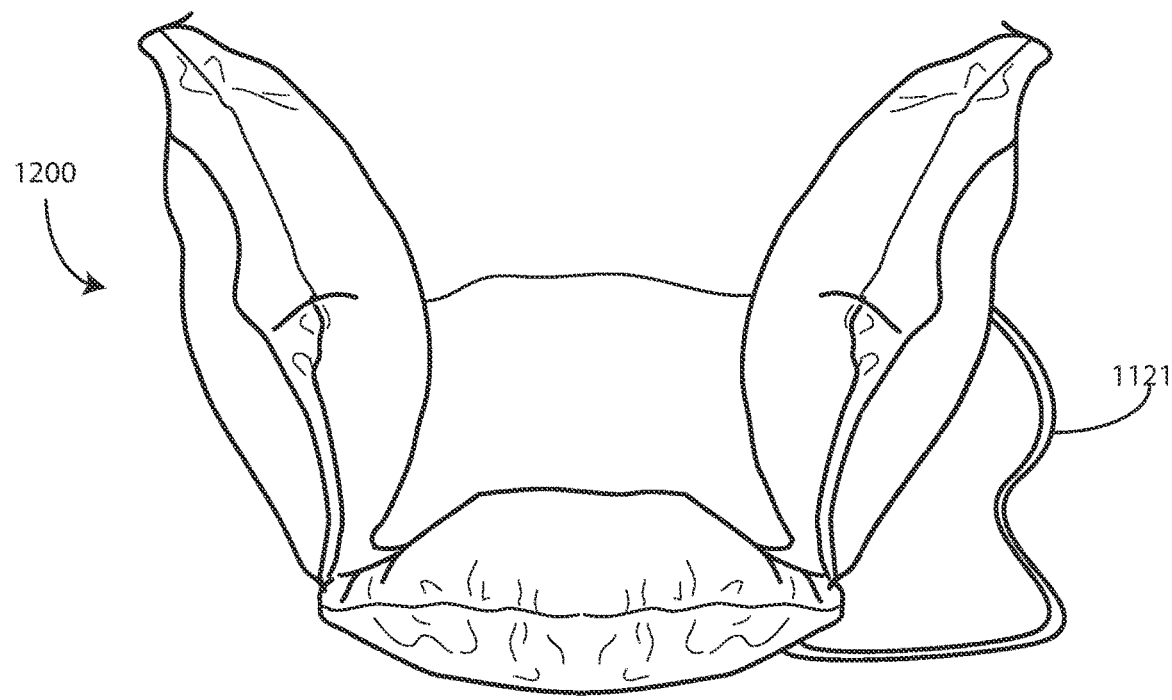
FIG. 12 illustrates a top plan view of another explanatory device in accordance with one or more embodiments of the disclosure.

The device 1100 can include one side member 1121, or two side members 1121,1122. For example, turning briefly to FIG. 12, one side member 1121 is included in a device 1200. By contrast, turning briefly to FIG. 13, two side members 1121,1122 are included in a device 1300. Turning now back to FIG. 11, the leg engaging section 101 includes one side member 1121 shown in solid lines, and another side member 1122 shown in dashed lines. This is to indicate that the device 1100 could have either one side member 1121 or two side members 1121,1122. Note where only one side member 1121 is included, the side member 1121 can be placed either on the medial side 109 or the lateral side 110 of the device 1100.

Figure 13:
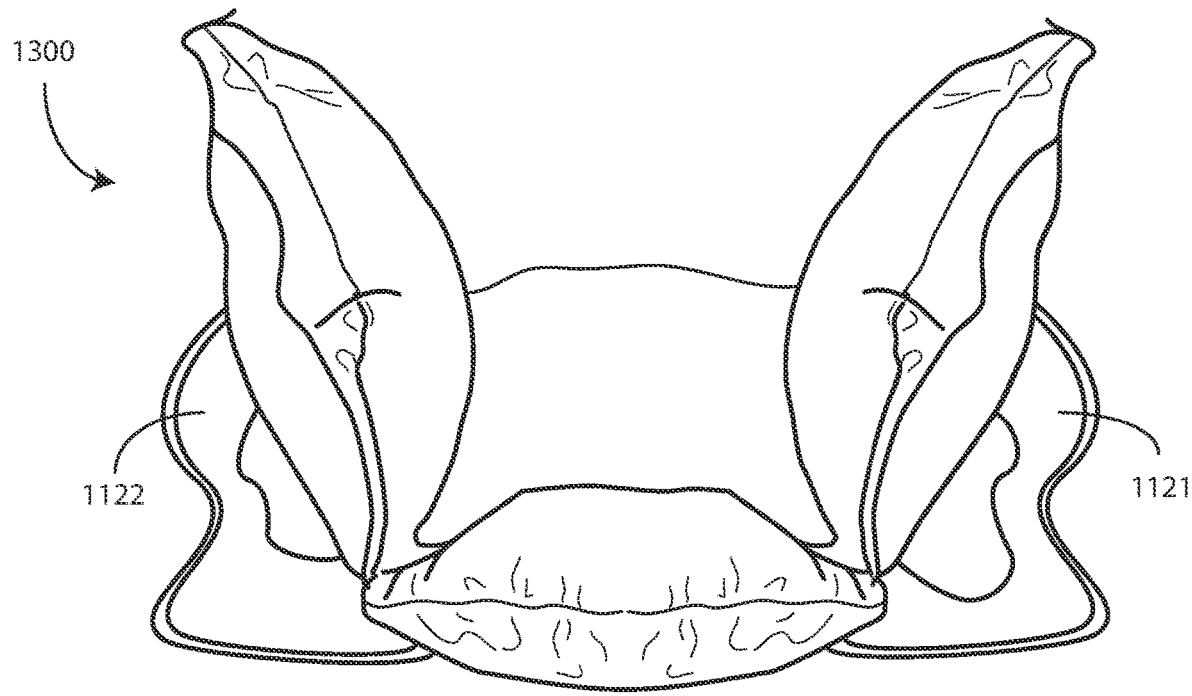
FIG. 13 illustrates a top plan view of yet another explanatory device in accordance with one or more embodiments of the disclosure.

In this embodiment, the leg engaging section 101 defines at least one aperture 1105,1106 at the side members 1121, 1122. An upper aperture 1105,1106 is shown in FIG. 11. However, the apertures could be disposed at the bottom of the side members in another embodiment, i.e., toward the heel receiver 103. In still another embodiment, the one or more side members 1121,1122 could have apertures on the top and the bottom as well (as shown in FIG. 13). The apertures 1105,1106 allow at least one bolster tube to be selectively insertable through, and removable from, the at least one aperture 1105,1106. The side members 1121,1122 thus advantageously allow the device 1100 to advantageously selectively, i.e., at the choice of the user, incorporate a bolster tube.

In one embodiment, a bolster tube can be inserted between the inner material 1103 and the outer material 1104 of the leg engaging section 101 along the side members 1121,1122. The device 1100 can thus be worn as a simple protective device at times. At other times, a health care services provider or a user may insert a bolster tube into one or more of the side members 1121,1122 to keep the device 1100 supported without the need of external stabilization devices such as pillow or stabilization wedge. The device 1100 of FIG. 11 advantageously allows the bolster tubes to be selectively removable through an aperture 1105,1106 such that they can be inserted into, and removed from, the inner material 1103 and the outer material 1104 of the leg engaging section 101.

The ability to selectively insert, and remove, bolster tubes through the apertures 1105,1106 of the leg engaging section 101 offers other advantages as well. For instance, in one or more embodiments, the bolster tubes can be manufactured in different sizes. Accordingly, a user or health care services provider can select a bolster tube of a particular size so as to provide a desired amount of stability. Inserting different sized tubes provides different amounts of stability.

Figure 14:
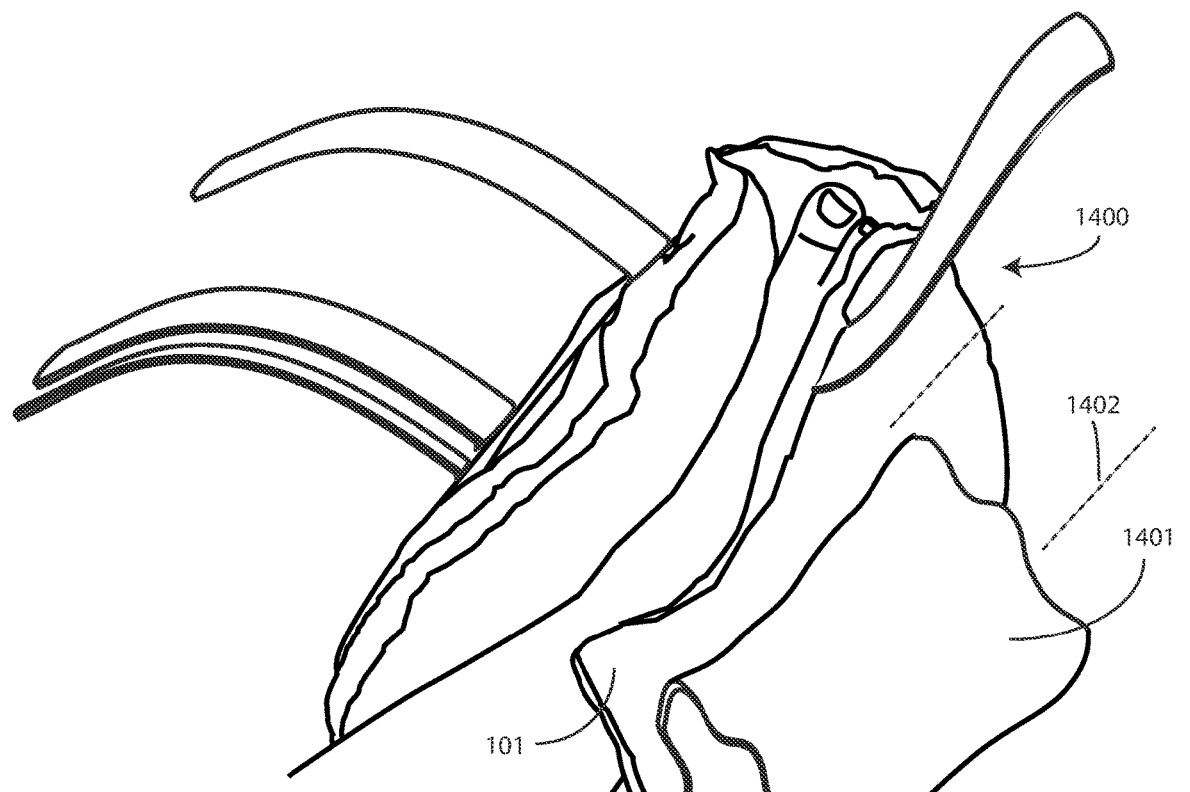
FIG. 14 illustrates an explanatory method step of using another explanatory device in accordance with one or more embodiments of the disclosure.
Figure 14:
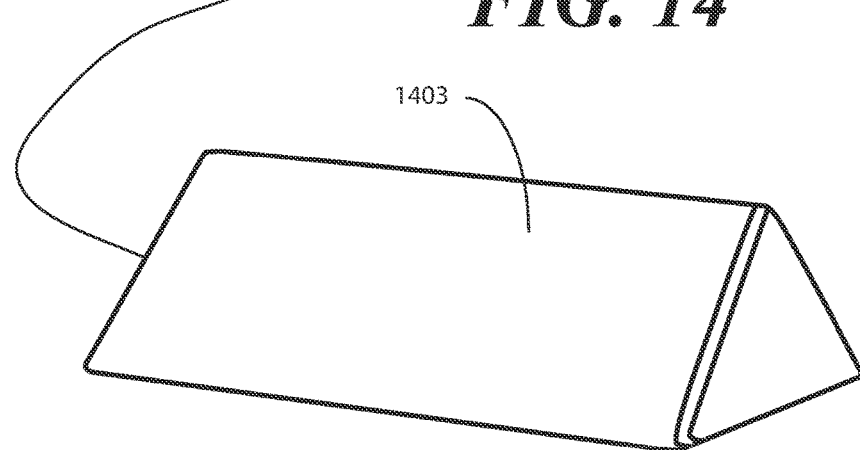
Figure 15:
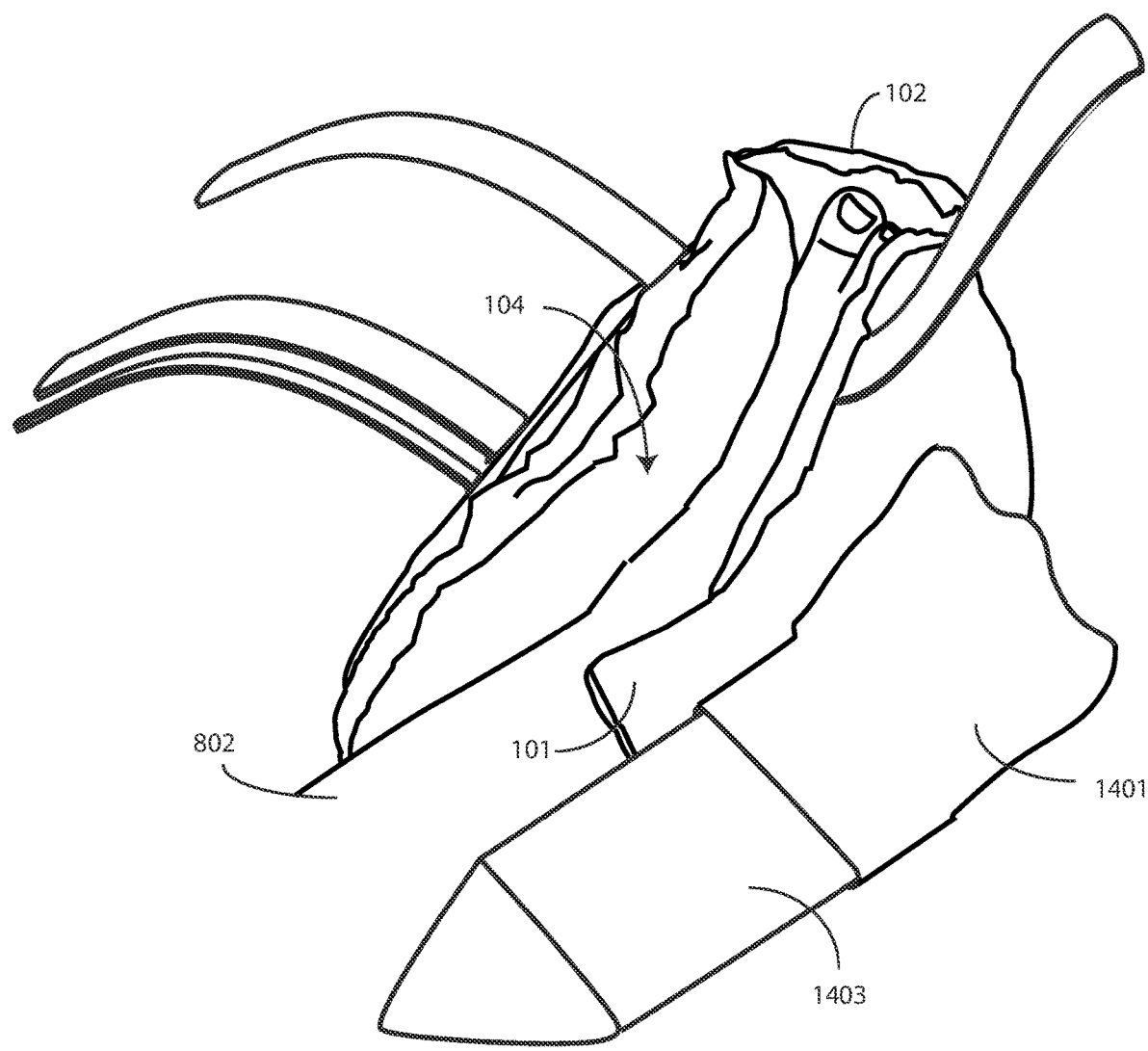
FIG. 15 illustrates another explanatory method step of using another explanatory device in accordance with one or more embodiments of the disclosure.
Figure 16:
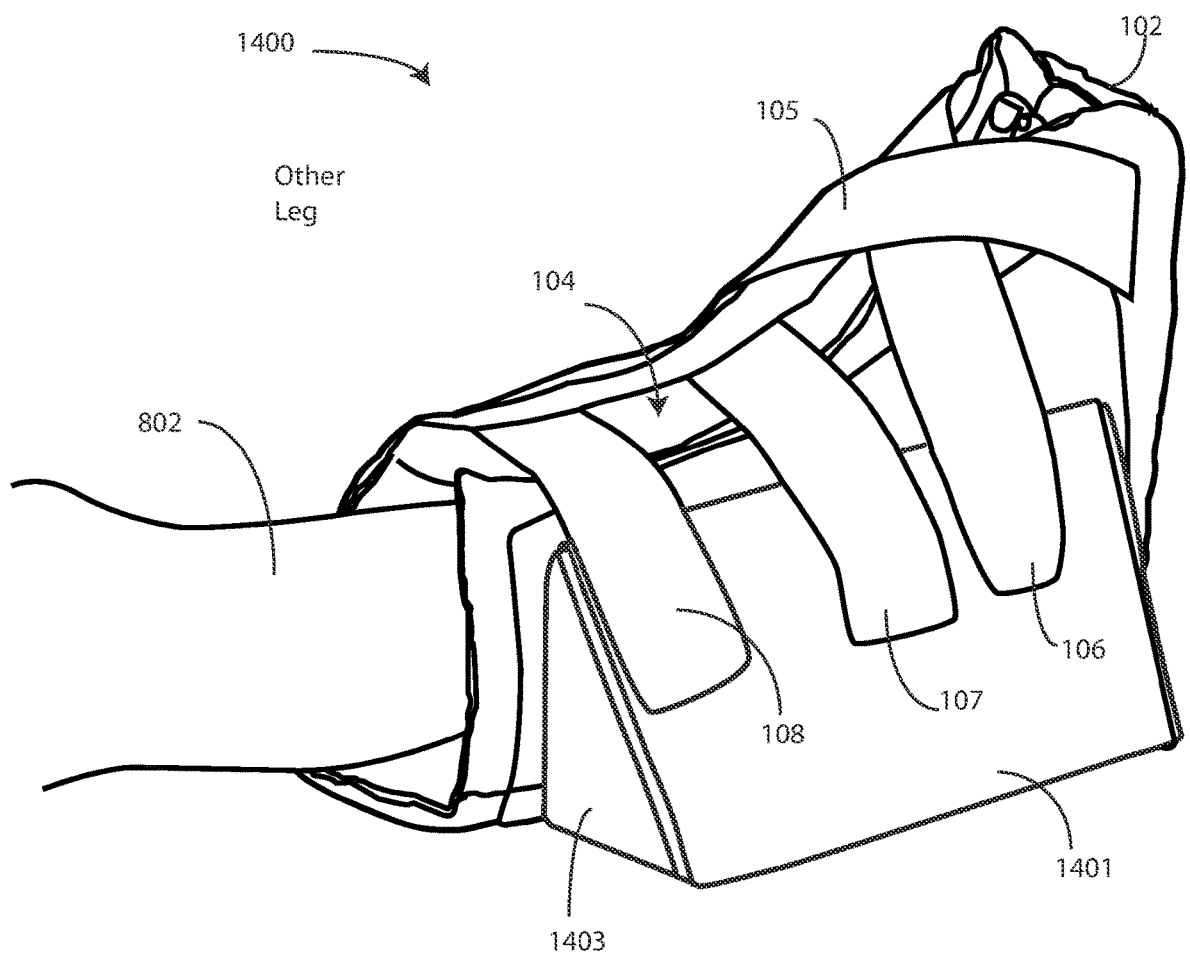
FIG. 16 illustrates another explanatory device in accordance with one or more embodiments of the disclosure in use.

Turning now to FIGS. 14-16, illustrated therein is a method of using another device 1400. Beginning with FIG. 14, the device 1400 includes a leg engaging section 101 that defines at least one exterior pocket 1401 having an axis 1402 oriented substantially parallel to the leg engaging section 101. In this illustrative embodiment, the pocket 1401 is to selectively receive a bolster 1403 to stabilize the device rotationally. The illustrative bolster 1403 of this embodiment has a triangular cross section.

While one exterior pocket 1401 is shown in FIG. 14, in another embodiment the device 1400 includes a first pocket and a second pocket as shown above with reference to FIG. 13. Where two pockets are included, the first pocket can be disposed along a first side of the leg engaging section 101, the second pocket can disposed along a second side of the leg engaging section 101, where the first side and the second side opposite sides of the device 1400.

Turning now to FIG. 15, a patient's leg 802 passes through the leg insertion aperture 104 disposed along the leg engaging section 101 and the foot engaging section 102 such that the patient's heel engages the heel receiver (103). Once this step is complete, the bolster 1403 is inserted into the exterior pocket 1401 to rotationally stabilize the device. Next, turning to FIG. 16, a health care services provider will wrap the fastening straps 105,106,107,108 across the leg insertion aperture 104 to retain the device 1400 to the patient's leg 802.

In this illustrative embodiment, fastening strap 105 and fastening strap 106 have been "crisscrossed." Fastening straps 107,108 could have been similarly crisscrossed, but have been left in a substantially parallel configuration in this illustrative embodiment. In one embodiment, the health care services provider is instructed to achieve this configuration as follows: after inserting the patient's leg 802 into the leg insertion aperture 104, fastening strap 108 is to be wrapped about the leg insertion aperture 104 and attached to a panel on the opposite side of the device 1400. Next, insertion strap 107 is to be wrapped about the leg insertion aperture 104 and attached to a panel on the opposite side of the device 1400 to securely affix the leg engaging section 101 about the patient's leg 802. While fastening straps 107,108 can be attached so that they are substantially parallel, in one embodiment the health care services provider is instructed to cause fastening strap 107 to extend toward the foot engaging section 102, and thereby non-parallel relative to fastening strap 108, to achieve a more snug fit.

Next, the health care services provider is instructed to wrap fastening strap 106 across the leg insertion aperture 104 in a substantially diagonal configuration to attach to a panel on the opposite side of the device 1400. Corresponding fastening strap 105 can then crisscross over fastening strap 106 to attach to the opposite panel. Fastening straps 105 and 106 work to retain the foot engaging section 102 to the patient's foot.

In the illustrative embodiment of FIG. 16, the patient's leg 802 is the right leg, and the bolster 1403 is disposed on the lateral side of the leg 802. Embodiments of the disclosure contemplate that a patient will have a tendency to roll their leg outwardly. Accordingly, in one embodiment, where one pocket 1401 and bolster 1403 are used, the device 1400 is configured such that when the patient's leg 802 is inserted into the leg insertion aperture 104, the leg 802 is disposed between the bolster 1403 and another leg of the patient. Other configurations will be obvious to those of ordinary skill in the art having the benefit of this disclosure.

In the foregoing specification, specific embodiments of the present disclosure have been described. However, one of ordinary skill in the art appreciates that various modifications and changes can be made without departing from the scope of the present disclosure as set forth in the claims below. Thus, while preferred embodiments of the disclosure have been illustrated and described, it is clear that the disclosure is not so limited. Numerous modifications, changes, variations, substitutions, and equivalents will occur to those skilled in the art without departing from the spirit and scope of the present disclosure as defined by the following claims. Accordingly, the specification and figures are to be regarded in an illustrative rather than a restrictive sense, and all such modifications are intended to be included within the scope of present disclosure. The benefits, advantages, solutions to problems, and any element(s) that may cause any benefit, advantage, or solution to occur or become more pronounced are not to be construed as a critical, required, or essential features or elements of any or all the claims.

What is claimed is:

1. A device, comprising:
 a leg engaging section intersecting a foot engaging section, the leg engaging section and the foot engaging section defining a leg insertion aperture, at least the leg engaging section comprising a compressible cushion layer; and
 at least one side member attached to the leg engaging section, the at least one side member allowing at least one bolster tube to be selectively inserted therein.

2. The device of claim 1, the at least one side member defining at least one aperture into which the at least one bolster tube may be selectively inserted.

3. The device of claim 2, the at least one aperture comprising a first aperture situated at a top of the at least one side member and a second aperture situated at a bottom of the at least one side member.

4. The device of claim 2, the at least one side member comprising a first side member and a second side member.

5. The device of claim 4, further comprising the at least one bolster tube.

6. The device of claim 5, wherein the at least one bolster tube comprises a first bolster tube and a second bolster tube.

7. The device of claim 6, wherein only the first bolster tube is inserted in one of the first side member or the second side member to stabilize the device rotationally.

8. The device of claim 7, wherein the first bolster tube has a different size than the second bolster tube.

9. The device of claim 6, wherein the first bolster tube is inserted in the first side member and the second bolster tube is inserted in the second side member.

10. The device of claim 9, wherein the first bolster tube and the second bolster tube have different sizes.

11. The device of claim 6, the first bolster tube disposed along a first side of the leg engaging section, the second bolster tube disposed along a second side of the leg engaging section.

12. The device of claim 11, the first bolster tube, the second bolster tube, and the leg engaging section arranged in a parallel alignment.

13. The device of claim 6, the leg engaging section defining a first side, a second side, and a base member disposed between the first side and the second side.

14. The device of claim 1, the at least one bolster tube defining a trapezoidal cross section.

15. The device of claim 1, the at least one bolster tube defining a polygonal cross section.

16. The device of claim 1, further comprising one or more fastening straps.

17. The device of claim 16, the one or more fastening straps comprising at least one fastening strap extending from a first side of the device and at least one other fastening strap extending from another side of the device.

18. A device, comprising:
a leg engaging section and a foot engaging section, the leg engaging section defining a leg insertion aperture, wherein:
the leg engaging section comprises a compressible cushion layer; and
the leg engaging section comprises a bolster inserted into a side member attached to the leg engaging section configured to stabilize the device rotationally.

19. The device of claim 18, further comprising the bolster.

20. The device of claim 18, the leg engaging section comprising a first bolster inserted into a first side member attached to a first side of the leg engaging section and a second bolster inserted into a second side member attached to a second side of the leg engaging section, the first side and the second side defining opposite sides of the device.

\* \* \* \* \*